(12) United States Patent
Walle-Jensen et al.

(10) Patent No.: US 12,193,645 B2
(45) Date of Patent: Jan. 14, 2025

(54) SYSTEMS AND METHODS FOR FLUORESCENCE VISUALIZATION

(71) Applicant: Stryker Corporation, Portage, MI (US)

(72) Inventors: Jørgen Walle-Jensen, Vancouver (CA); Paul Roald Westwick, Vancouver (CA); Vivian Wing Yan Wong, Vancouver (CA); Justin Winston Junyick Choy, Vancouver (CA)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 17/478,867

(22) Filed: Sep. 17, 2021

(65) Prior Publication Data

US 2022/0087518 A1 Mar. 24, 2022

Related U.S. Application Data

(60) Provisional application No. 63/080,641, filed on Sep. 18, 2020.

(51) Int. Cl.
*A61B 1/00* (2006.01)
*A61B 1/04* (2006.01)
*A61B 1/06* (2006.01)

(52) U.S. Cl.
CPC .......... *A61B 1/043* (2013.01); *A61B 1/00039* (2013.01); *A61B 1/00045* (2013.01); *A61B 1/06* (2013.01)

(58) Field of Classification Search
CPC .............. A61B 1/0638; A61B 1/00186; A61B 1/00057; A61B 1/043; A61B 1/00137;
(Continued)

(56) References Cited

U.S. PATENT DOCUMENTS 9,872,610 B2   1/2018  Higuchi
2002/0093563 A1 * 7/2002  Cline ................. A61B 1/00009
                                         600/101
(Continued)

FOREIGN PATENT DOCUMENTS

EP          3050485 A1    8/2016
JP       2000-325295 A   11/2000
(Continued)

OTHER PUBLICATIONS

International Preliminary Report on Patentability dated Mar. 21, 2023, directed to International Application No. PCT/CA2021/051304; 4 pages.
(Continued)

*Primary Examiner* — Timothy J Neal
(74) *Attorney, Agent, or Firm* — Morrison & Foerster LLP

(57) ABSTRACT

A method for fluorescence imaging includes receiving first fluorescence imaging data, receiving a user input selecting a reference region associated with the first fluorescence imaging data, determining a reference fluorescence intensity level based on the reference region, receiving second fluorescence imaging data, determining a relative fluorescence intensity level of a region associated with the second fluorescence imaging data that is relative to the reference fluorescence intensity level, and displaying an indication of the relative fluorescence intensity level.

23 Claims, 9 Drawing Sheets
(2 of 9 Drawing Sheet(s) Filed in Color)

(58) Field of Classification Search
CPC ............. A61B 1/0005; A61B 1/0655; A61B 1/000095; A61B 1/042; A61B 1/0669; A61B 1/00045; A61B 1/00114; A61B 1/00117; A61B 1/00078; A61B 1/00105; A61B 1/00039; A61B 1/06; H04N 23/71; H04N 23/74; H04N 23/555
See application file for complete search history.

(56) References Cited

U.S. PATENT DOCUMENTS

| | | | |
|---|---|---|---|
| 2004/0010195 A1* | 1/2004 | Zelenchuk | A61B 5/0075 600/476 |
| 2004/0019253 A1* | 1/2004 | Tsujita | A61B 1/04 600/109 |
| 2010/0061604 A1* | 3/2010 | Nahm | G06T 7/90 250/363.01 |
| 2011/0071353 A1* | 3/2011 | Ozawa | A61B 1/0653 600/109 |
| 2011/0178412 A1* | 7/2011 | Orlewski | A61B 5/0071 600/477 |
| 2016/0157763 A1* | 6/2016 | Tominaga | A61B 1/0646 600/317 |
| 2016/0253800 A1* | 9/2016 | Gurevich | G16H 50/50 382/128 |
| 2016/0262602 A1 | 9/2016 | Yu | |
| 2017/0084012 A1* | 3/2017 | Walle-Jensen | G16H 50/30 |
| 2017/0084024 A1* | 3/2017 | Gurevich | A61B 5/7239 |
| 2017/0086659 A1* | 3/2017 | Uchiyama | A61B 1/07 |
| 2018/0160916 A1* | 6/2018 | Madsen | A61B 17/1114 |
| 2019/0180439 A1* | 6/2019 | Wood | G06T 3/0068 |
| 2019/0183357 A1 | 6/2019 | Godavarty | |
| 2020/0150041 A1* | 5/2020 | Harootunian | G06T 7/136 |
| 2020/0237937 A1* | 7/2020 | Ralph | G06T 7/0012 |
| 2020/0281542 A1* | 9/2020 | Irish | A61B 5/7495 |
| 2021/0007687 A1* | 1/2021 | Gurevich | G06T 7/0012 |
| 2021/0100461 A1* | 4/2021 | Lund | G16H 50/50 |
| 2021/0259625 A1* | 8/2021 | Saiko | A61B 5/445 |
| 2021/0275088 A1* | 9/2021 | Fleury | A61B 5/489 |

FOREIGN PATENT DOCUMENTS

| | | |
|---|---|---|
| WO | 2016/123705 A1 | 8/2016 |
| WO | 2017/051229 A1 | 3/2017 |

OTHER PUBLICATIONS

International Search Report and Written Opinion mailed Dec. 20, 2021, directed to International Application No. PCT/CA2021/051304; 6 pages.

Extended European Search Report dated Jul. 2, 2024, directed to EP Application No. 21867996.7; 13 pages.

Partial Supplementary European Search Report dated Apr. 10, 2024, directed to EP Application No. 21867996.7; 15 pages.

* cited by examiner

SYSTEMS AND METHODS FOR FLUORESCENCE VISUALIZATION

CROSS-REFERENCE TO RELATED APPLICATIONS

This application claims the benefit of U.S. Provisional Application No. 63/080,641, filed Sep. 18, 2020, the entire contents of which are hereby incorporated by reference herein.

FIELD

The present disclosure relates generally to medical imaging, and more particularly to fluorescence imaging for visualizing blood flow in tissue of a subject.

BACKGROUND

Medical imaging systems (e.g., endoscopic imaging systems for minimally invasive surgery or open field medical imaging systems) can help provide clinical information to medical practitioners making decisions (e.g. intraoperative or treatment decisions) based on attributes of tissue of a subject. In many instances, it is useful for medical imaging systems to provide fluorescence imaging for visualizing tissue or attributes of tissue that cannot be visualized or are poorly visualized with white light imaging. Fluorescence imaging generally involves the administration of a bolus of an imaging agent that circulates through the subject's tissue and emits a fluorescence signal when illuminated with the appropriate excitation light. A fluorescence imaging system acquires images of the fluorescence signal emitted by the imaging agent as the bolus passes through the subject's tissue in the imaging field of view. The fluorescence images may be used to make qualitative or quantitative assessments of attributes of the tissue under observation.

SUMMARY

According to various aspects, systems and methods disclosed herein can enable a user to set a reference region in fluorescence imaging and provide a visual indication of a relative fluorescence intensity in the fluorescence imaging based on the user selected reference. Optionally, the visual indication is a relative level of fluorescence intensity in a user selected target region, which can be associated with a different region of tissue than the reference region or with the same region of tissue but at a different time in the imaging session. In other embodiments, the visual indication is a color map in which the color scale for the color map is tied to the user selected reference. By providing the user with the ability to set a reference intensity level, the systems and methods can enable the user to more easily assess the relative states of a target region.

According to various aspects, a method for fluorescence imaging includes receiving first fluorescence imaging data, receiving a user input selecting a reference region associated with the first fluorescence imaging data, determining a reference fluorescence intensity level based on the reference region, receiving second fluorescence imaging data, determining a relative fluorescence intensity level of a region associated with the second fluorescence imaging data that is relative to the reference fluorescence intensity level, and displaying an indication of the relative fluorescence intensity level.

Optionally, determining the reference fluorescence intensity level may include determining a mean fluorescence intensity in the reference region and determining the relative fluorescence intensity level may include determining a mean fluorescence intensity in the region associated with the second fluorescence imaging data.

Optionally, the method can further include displaying a visualization based on the first fluorescence imaging data, wherein the user input selecting the reference region is a user input selecting a region of the visualization.

Optionally, the visualization can include video.

Optionally, the visualization can include fluorescence overlay on visible light imaging.

Optionally, receiving a user input selecting a reference region can include locating a graphical selector at tissue captured in the first fluorescence imaging data to select a reference region of the tissue.

Optionally, the reference region of the tissue can be healthy tissue.

Optionally, the indication of the relative fluorescence intensity level can be a numerical indication.

Optionally, the method can further include receiving third fluorescence imaging data and updating the indication of the relative fluorescence intensity level based on the third fluorescence imaging data.

Optionally, the method can further include providing an indication of when the reference fluorescence intensity level was determined.

Optionally, the first and second fluorescence imaging data can include video frames.

Optionally, the method can further include determining multiple relative fluorescence intensity levels based on multiple regions associated with the second fluorescence imaging data.

Optionally, the reference region and the region associated with the second fluorescence imaging data can be associated with the same region of tissue such that the relative fluorescence intensity level indicates a change in fluorescence intensity over time for the region of tissue.

Optionally, the first and second fluorescence imaging data can be received from an imager during a medical procedure.

Optionally, the first and second fluorescence imaging data can include normalized fluorescence intensity data.

According to various aspects, a system for fluorescence imaging includes one or more processors, memory, and one or more programs, wherein the one or more programs are stored in the memory and configured to be executed by the one or more processors, the one or more programs including instructions for: receiving first fluorescence imaging data, receiving a user input selecting a reference region associated with the first fluorescence imaging data, determining a reference fluorescence intensity level based on the reference region, receiving second fluorescence imaging data, determining a relative fluorescence intensity level of a region associated with the second fluorescence imaging data that is relative to the reference fluorescence intensity level, and displaying an indication of the relative fluorescence intensity level.

Optionally, the system can include an imager for generating the first and second fluorescence imaging data.

Optionally, the system can include an illuminator for generating fluorescence excitation light.

Optionally, selecting the target region can include receiving a user input to select the target region.

Optionally, the first and second fluorescence imaging data can include normalized fluorescence intensity data.

According to various aspects, a method for fluorescence imaging includes receiving fluorescence imaging data, receiving a user input selecting a reference region associated with the fluorescence imaging data, determining a reference fluorescence intensity level based on the reference region, and displaying a color map based on the fluorescence imaging data, wherein a color scale of the color map is based on the reference fluorescence intensity level.

Optionally, an upper end of the color scale can be associated with the reference fluorescence intensity level.

Optionally, determining the reference fluorescence intensity level can include determining a mean fluorescence intensity in the reference region.

Optionally, the method may further include receiving the user input while the color map is displayed and adjusting the color scale of the color map in response to the user input selecting the reference region.

Optionally, the fluorescence imaging data can be video data.

Optionally, displaying the color map can include displaying the color map as an overlay on visible light imaging.

Optionally, receiving the user input selecting a reference region can include moving a graphical selector relative to the color map.

Optionally, the color map can be selected from a plurality of predetermined color maps associated with different procedures.

Optionally, the color scale can include a geometric scale in fluorescence intensity levels between colors.

Optionally, the color scale can be a linear scale between colors.

Optionally, the color scale can be a nonlinear scale between colors.

Optionally, the color scale includes a combination of one or more of a linear, a geometric, and a nonlinear portion of a scale in fluorescence intensity levels between colors.

Optionally, an end of the color scale can correspond to a grey color.

Optionally, the fluorescence imaging data can be received from an imager during a medical procedure.

Optionally, the fluorescence imaging data can include endoscopic imaging data or open-field imaging data.

Optionally, the fluorescence imaging data can include normalized fluorescence intensity data.

According to various aspects, a system for fluorescence imaging includes one or more processors, memory, and one or more programs, wherein the one or more programs are stored in the memory and configured to be executed by the one or more processors, the one or more programs including instructions for: receiving fluorescence imaging data, receiving a user input selecting a reference region associated with the fluorescence imaging data, determining a reference fluorescence intensity level based on the reference region, and displaying a color map based on the fluorescence imaging data, wherein a color scale of the color map is based on the reference fluorescence intensity level.

Optionally, the system may further include an imager for generating the first and second fluorescence imaging data.

Optionally, the system may further include an illuminator for generating fluorescence excitation light.

Optionally, the fluorescence imaging data may include normalized fluorescence intensity data.

According to various aspects, a non-transitory computer readable storage medium stores one or more programs for execution by one or more processors of a fluorescence imaging system, the one or more programs comprising instructions for performing any of the methods described above.

According to various aspects, a system for fluorescence imaging includes one or more processors, memory, and one or more programs, wherein the one or more programs are stored in the memory and configured to be executed by the one or more processors, the one or more programs including instructions for performing any of the methods described above.

BRIEF DESCRIPTION OF THE FIGURES

The patent or application file contains at least one drawing executed in color. Copies of this patent or patent application publication with color drawing(s) will be provided by the Office upon request and payment of the necessary fee. The invention will now be described, by way of example only, with reference to the accompanying drawings, in which.

DETAILED DESCRIPTION

Figure 1:
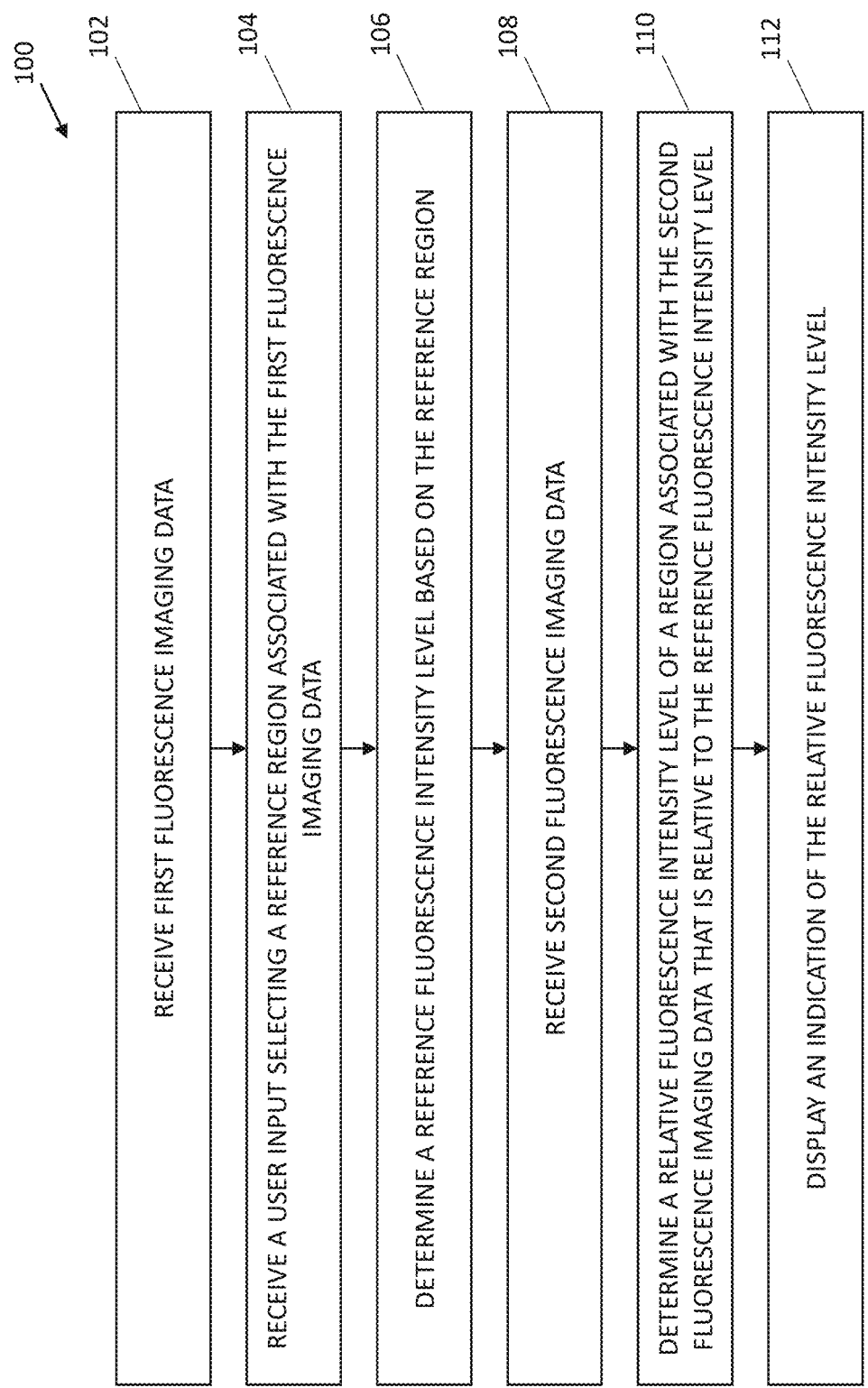
FIG. 1 is an exemplary flow diagram for fluorescence visualization based on a user selection of a reference fluorescence intensity.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Systems and methods described herein enable fluorescence imaging visualization in which a user can define a reference level of fluorescence intensity to facilitate direct comparisons between target fluorescence levels and the reference fluorescence levels. According to various aspects, fluorescence imaging data is received, a user selects a reference region based on the fluorescence imaging data, a reference fluorescence intensity value is determined, and the reference fluorescence intensity value is used to provide a display that indicates a level of fluorescence intensity in one or more regions of interest relative to the reference level of intensity. Optionally, this can be a numeric value associated with a target region of interest. In other embodiments, this can be a color map scaled based on the reference intensity level. According to various aspects, the reference region can be set once and relative fluorescence intensity indications (numeric, color map, or otherwise) can be updated as new fluorescence imaging data is generated, such as over the course of a fluorescence imaging session. According to various aspects, this can provide real-time relative fluorescence intensity information to the user.

Optionally, the fluorescence imaging data may comprise normalized fluorescence intensity data. For example, the normalized fluorescence intensity data may be normalized on a pixel-by-pixel basis such as based on reflectance imaging, or on a global basis such as based on one or more signals from a photo diode or other light sensor. The normalization may, for example, normalize the fluorescence intensity data for imaging working distance and/or for variation of the illumination profile across the imaging field of view.

In the following description, reference is made to the accompanying drawings, in which are shown, by way of illustration, specific examples that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates a method 100 for fluorescence imaging visualization and providing an indication of a relative level of fluorescence based on a user selected reference region. Method 100 is performed based on fluorescence imaging data generated by a fluorescence imaging system and can be performed by the fluorescence imaging system or any computing system communicatively coupled to a fluorescence imaging system that receives fluorescence imaging data from the fluorescence imaging system.

Method 100 can be performed after the administration of a bolus of a fluorescence imaging agent to a patient and based on fluorescence imaging data generated using a fluorescence imager that has tissue of interest of a subject within its field of view. Depending on the procedure, the tissue of interest can be imaged during an invasive procedure, such as a minimally invasive procedure using an endoscopic imager or an open procedure using an open-field imager, or via a non-invasive procedure, such as involving through-the-skin imaging.

At step 102, first fluorescence imaging data is received at one or more processors. The fluorescence imaging data can include a single fluorescence image and/or a time series of fluorescence images (which includes video frames). The fluorescence imaging data can be received as the fluorescence imaging data is generated (i.e., "in real time"). The fluorescence imaging data can be received directly from a fluorescence imager or from any suitable component of a fluorescence imaging system, such as from a camera control unit, or from a system that processes imaging data from the imaging system. The imaging data is received at one or more processors that can be or include one or more processors of the imaging system, including one or more processors of the imager itself, or one or more processors of a computing system that is communicatively connected to the imaging system. Optionally, each fluorescence image frame generated by the fluorescence imager is received at step 102, or a subset (e.g., every other, every tenth, etc.) of the fluorescence image frames generated by the fluorescence imager are received at step 102.

At step 104, a user input is received that selects a reference region associated with the first fluorescence imaging data. For example, a fluorescence image, video, a fluorescence overlay on visible light imaging, or other type of visualization associated with imaged tissue may be displayed to the user and the user may select a reference region of the field of view. The reference region may be a region of tissue captured in the fluorescence imaging data that a user may deem appropriate to use for setting a reference fluorescence intensity. For example, a user may be interested in using as a reference fluorescence intensities associated with healthy levels of blood flow and/or tissue perfusion and may select a region in the visualization that has relative high fluorescence intensity.

The user may select a reference region using any suitable user input. Optionally, a graphical selector, such as a box or pointer, is provided to assist a user in selecting a reference region. The user may provide a selection input, such as a button press on an imager head, when the visual aid is located at the desired region of the visualization. Optionally, the visual aid is a box, or other bounded shape, located in a fixed position on a display screen and the user moves the imager relative to the tissue being imaged until the box is positioned over the region of tissue that the user desires to select as a reference region. Optionally, a reference region may be set by the user drawing an outline around the desired reference region.

At step 106, a reference fluorescence intensity level is determined based on the reference region. An example of a reference fluorescence intensity level is a mean fluorescence intensity in the reference region. Optionally, the reference fluorescence intensity level is determined based on a single fluorescence image. For example, a fluorescence image may be displayed, the user may select a reference region of the image, and the reference fluorescence intensity level may be determined based on the pixel values in the fluorescence image. As another example, a fluorescence video may be displayed, a user may select a reference region based on the video, and the reference fluorescence intensity level may be determined based on a single frame of the fluorescence video. The fluorescence intensity level may be determined based on multiple fluorescence images, such as based on an average of a predetermined number of fluorescence video frames.

At step 108, second fluorescence imaging data may be received. The second fluorescence imaging data is temporally sequential to the first fluorescence imaging data. For example, the first fluorescence imaging data may be an earlier portion of a florescence video stream and the second fluorescence imaging data may be a later portion of the fluorescence video stream.

At step 110, a relative fluorescence intensity level of a region associated with the second fluorescence imaging data is determined based on the reference fluorescence intensity level. The relative fluorescence intensity level corresponds to a level of fluorescence intensity of the region relative to the reference fluorescence intensity level determined at step 106. For example, a mean fluorescence intensity can be determined for a region associated with the second fluorescence imaging data and a ratio of the determined mean fluorescence intensity to the reference fluorescence intensity level can be calculated.

Optionally, the region associated with the second imaging data corresponds to the same region of tissue as the reference region. For example, a user may set a region in the field of view as a reference region and relative fluorescence intensity levels can be determined for that same region in the field of view for later generated fluorescence imaging data to provide an indication in the relative change in fluorescence intensity over time.

Optionally, the region associated with the second imaging data corresponds to a different region of tissue. For example, the user may select a target region for determining a relative fluorescence intensity level and the target region may correspond to a different region of tissue than the reference region. The user may select the target region in any suitable way, such as in similar fashion to the manner of selecting the reference region.

Optionally, the relative fluorescence intensity of the region associated with the second fluorescence imaging data is determined in response to a user input, which can include a user selection of a target region or can be simply a user command that the relative fluorescence intensity be determined. Optionally, the relative fluorescence intensity is determined automatically, without requiring a user input.

At step 112, an indication of the relative fluorescence intensity level determined at step 110 is displayed. The indication can be, for example, a numerical indication, such as a ratio or percentage. The indication can be any other suitable visual indication including, for example, based on a color scale indicating a higher, lower, or equal relative intensity.

According to various aspects, steps 108-112 may be performed continuously as new fluorescence imaging data is generated and/or received, including in real-time. So, for example, third imaging data may be received, and the indication of the relative fluorescence intensity level may be updated based on the intensity values in the third fluorescence imaging data.

Optionally, the user may select new or different target regions over time. Optionally, steps 110 and 112 are performed continuously as a user moves a target region selector (e.g., a pointer or box) relative to imaged tissue. For example, as a user drags or otherwise moves a selection box across the display screen, the indication may be updated according to a current region. Optionally, the region is associated with a fixed position in the field of view and the imager is moved relative to the tissue to determine a relative fluorescence intensity that corresponds to a different region of the tissue. For example, a selection box may be located in the center of the field of view and the user may observe the relative level of fluorescence intensity in a different region of tissue by moving the imager relative to the tissue such that the center of the field of view is positioned on the desired region of tissue. Optionally, a user may select multiple target regions and a relative fluorescence intensity level may be determined for each target region, with each being determined based on the same reference region selected in step 104.

Optionally, a visual indication associated with the reference region may be provided to indicate to the user when and/or where the reference region was defined. For example, a box may be positioned in the visualization in a position corresponding to the location of the reference region. Optionally, a time indication may be provided that indicates when the reference region was defined. The time can be an absolute time or a relative time, such as a timer running since the reference region was defined, or the time after first detecting fluorescence in the fluorescence imaging data at which the reference region was defined.

According to various aspects, the user can cancel the previously defined reference region and define a new reference region.

Using method 100, a user can easily compare a target region of tissue with a selected reference region. So, a user could set as the reference region a portion of the field of view associated with healthy tissue and the user can determine the level of blood flow and/or tissue perfusion in other portions of tissue relative to the healthy tissue to easily determine how healthy or not healthy other portions of tissue may be based on their relative blood flow and/or tissue perfusion.

Figure 2:
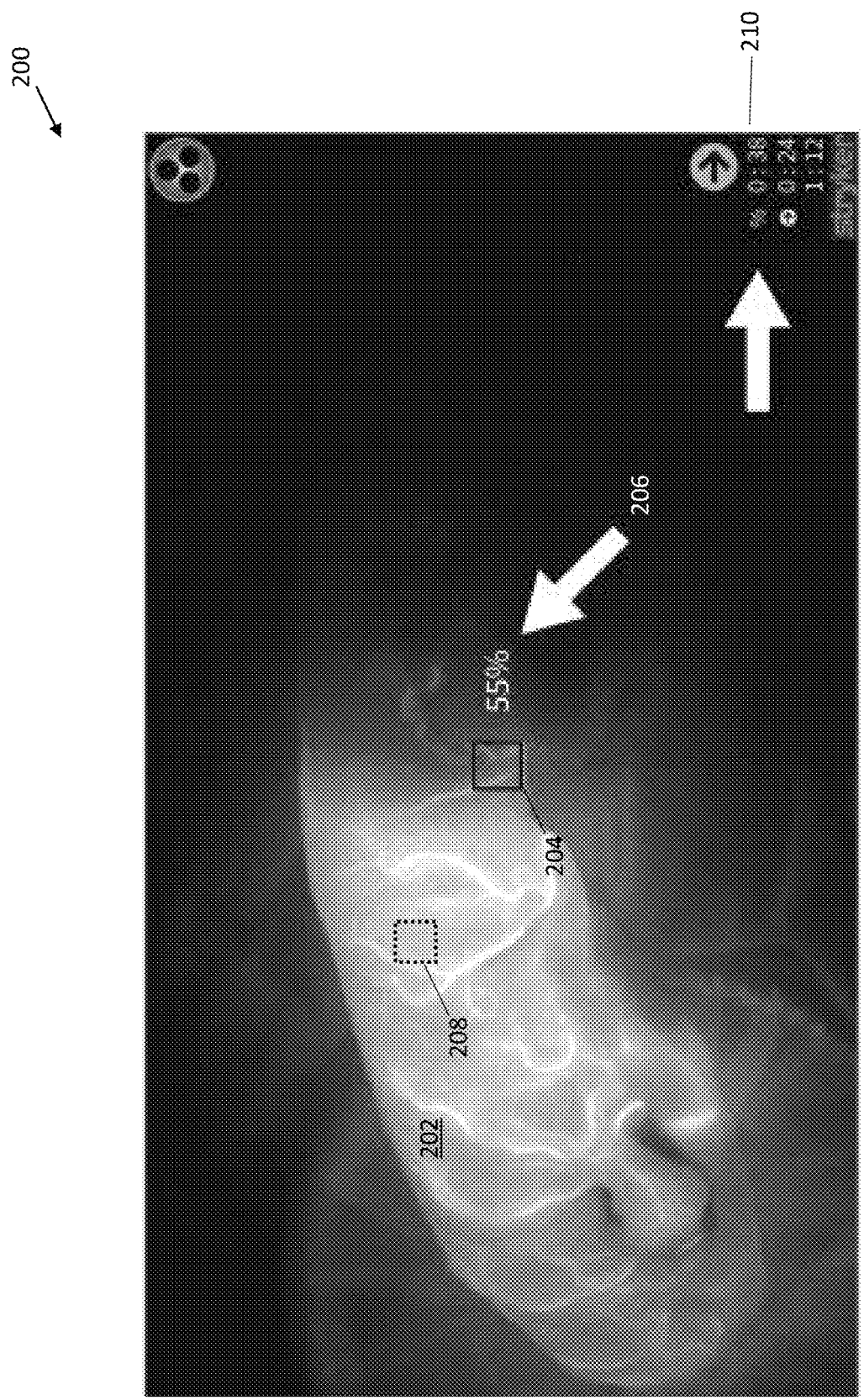
FIG. 2 is an exemplary fluorescence imaging visualization illustrating a user selection of a reference region.

FIG. 2 illustrates an exemplary graphical user interface 200 comprising a visualization 202 based on fluorescence imaging data, which can be, for example, a fluorescence image or video. The visualization 202 provides the fluorescence response of tissue within the field of view of an imager. A visual indicator of a target region 204 is provided and an indication 206 of a relative level of intensity of the target region relative to a reference region is displayed in the form of a percentage. In this example, the reference region 208 is indicated by a dashed box. Thus, in the illustrated example, the target region 204 has a level of intensity that is 55% of a level of intensity of the reference region. The level of intensity of the reference region can be the current level of intensity in the reference region or can be the level of intensity of the reference region at the time that the reference region was selected.

According to various aspects, the time 210 that the reference region was set may be displayed in the graphical user interface 200, which in the illustrated example is 38 seconds since a fixed starting point, which can be the start of the imaging session or the start of the relative fluorescence intensity calculation mode.

Figure 3:
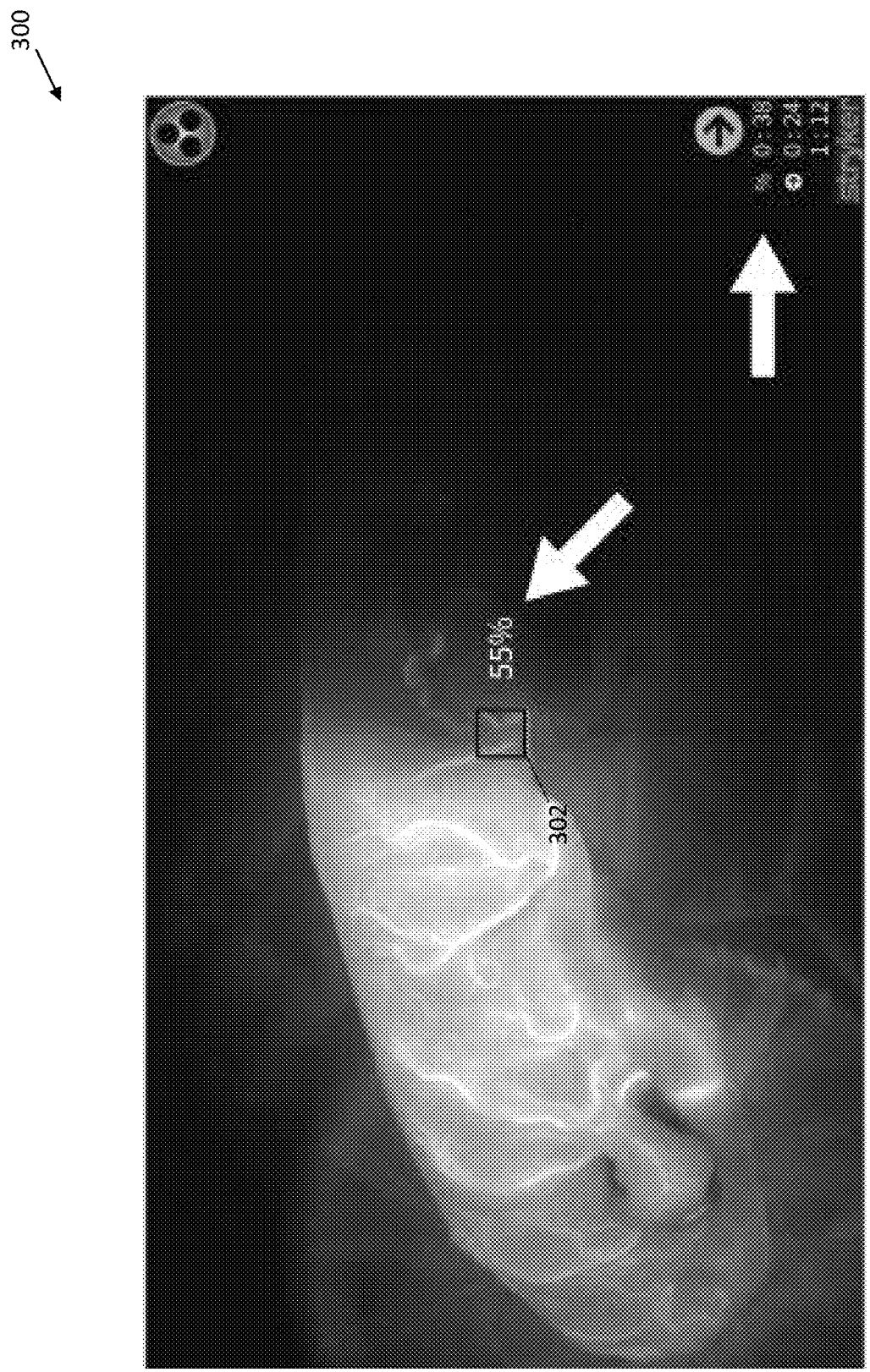
FIG. 3 is an exemplary fluorescence imaging visualization illustrating overlapping reference and target regions.

FIG. 3 illustrates an exemplary graphical user interface 300 that is similar to graphical user interface 200 but in which the reference region and the region for determining the relative fluorescence intensity level are both set by a fixed location of the field of view, which in the illustrated example is a box 302 in the center of the field of view. The user may select as a reference region a region within the field of view that is associated with a desired region of tissue by moving the imager relative to the tissue until the box 302 is aligned with the tissue. The user may then provide a selection command. Once the reference intensity level is set based on the user's selection command, the system may determine the relative fluorescence intensity based on the portion of the imaging data associated with that same centrally located box 302. If the imager is held in place, the relative fluorescence intensity level may indicate a change over time of the fluorescence intensity in the region of tissue aligned with the box 302. If, however, the imager is moved around relative to the tissue, the relative fluorescence intensity level will be associated with a different region of the tissue. Thus, according to various aspects, the user can select a target region by moving the imager relative to the tissue until the box 302 is aligned with the target tissue.

Optionally, the user can move box 302 relative to the field of view, such as by dragging the box across the screen via a suitable user input.

Figure 4:
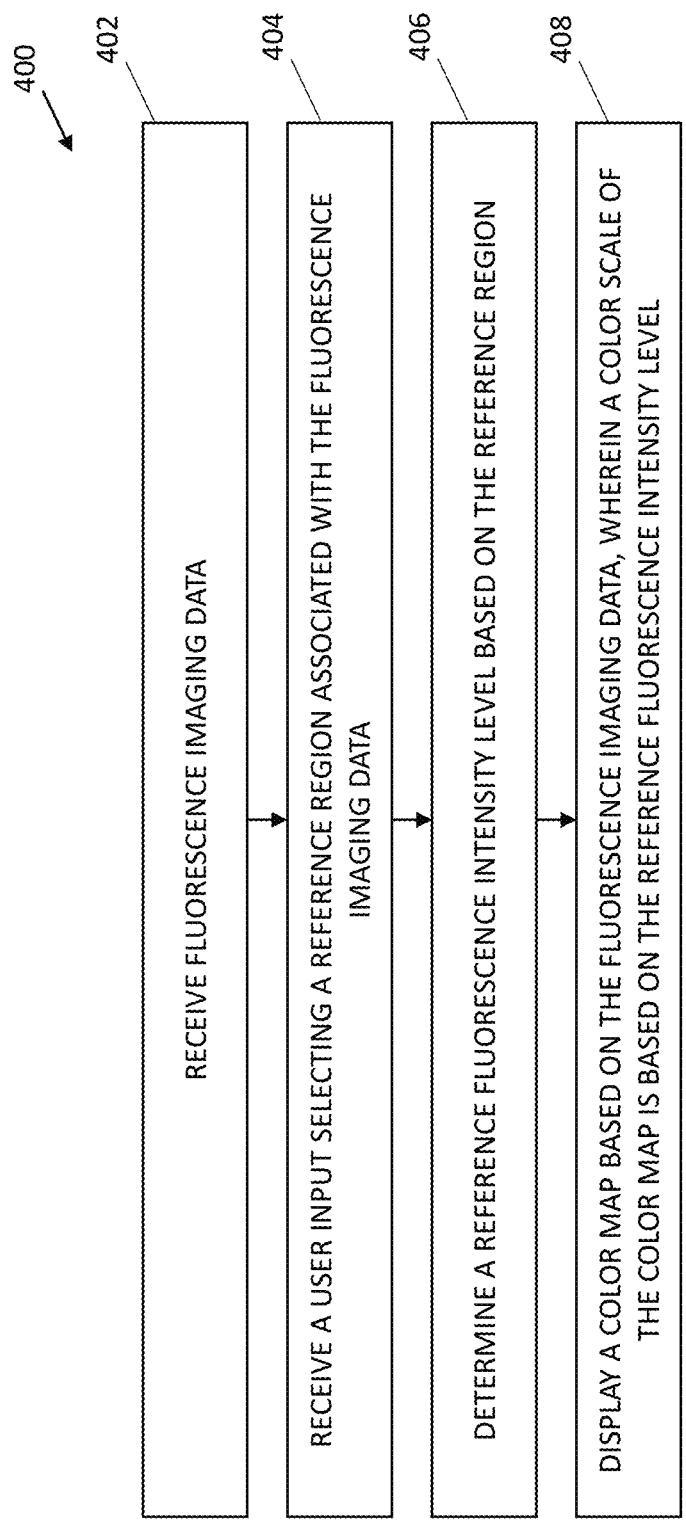
FIG. 4 is an exemplary flow diagram for a method for adjusting a fluorescence imaging based color map based on a user selected reference region.

FIG. 4 illustrates a method 400 for fluorescence visualization in which the colors of a color map are based on a user selected reference region. At step 402, fluorescence imaging data is received. Similarly to method 100, this can be a single fluorescence image or a series of fluorescence imaging frames.

At step 404, a user input is received that selects a reference region associated with the fluorescence imaging data. Step 404 can be performed in similar fashion to step 104 of method 100. At step 406, a reference fluorescence intensity level is determined based on the reference region selected in step 404. The reference fluorescence intensity level can be determined in similar fashion to step 106 of method 100.

At step 408, a color map that is generated from the fluorescence imaging data is displayed in which the color scale of the color map is based on the reference fluorescence intensity level determined in step 406. For example, a predetermined position on the scale may be set as equal to the reference fluorescence intensity level. The reference fluorescence intensity level can be used to set any suitable portion of the color scale. Optionally, the midpoint of the scale is set to the reference fluorescence intensity. Optionally, a minimum of the scale is set to the reference fluorescence intensity such that any intensity value below the reference value is the same color as that for the reference value. Optionally, a maximum of the scale is set to the reference fluorescence intensity such that any intensity value above the reference value is the same color as that for the reference value. Any other point of the scale can be set to the reference value, including, for example, the 75% point or the 90% point, etc.

The color map can be a gray-scale color map or a color spectrum color map. The color map may be displayed as an overlay on a visible light image. The color map may be updated as new fluorescence imaging data is generated and/or received.

Optionally, the color map is displayed prior to step 404 such that the user input may be informed by the color map. For example, the user may select a reference region by moving a graphical selector relative to the displayed color map. Upon the user selection of the reference region (such as via a user interface on the imager or any other suitable user interface), the color scale, and thus the color map, may be updated accordingly.

Figure 5:
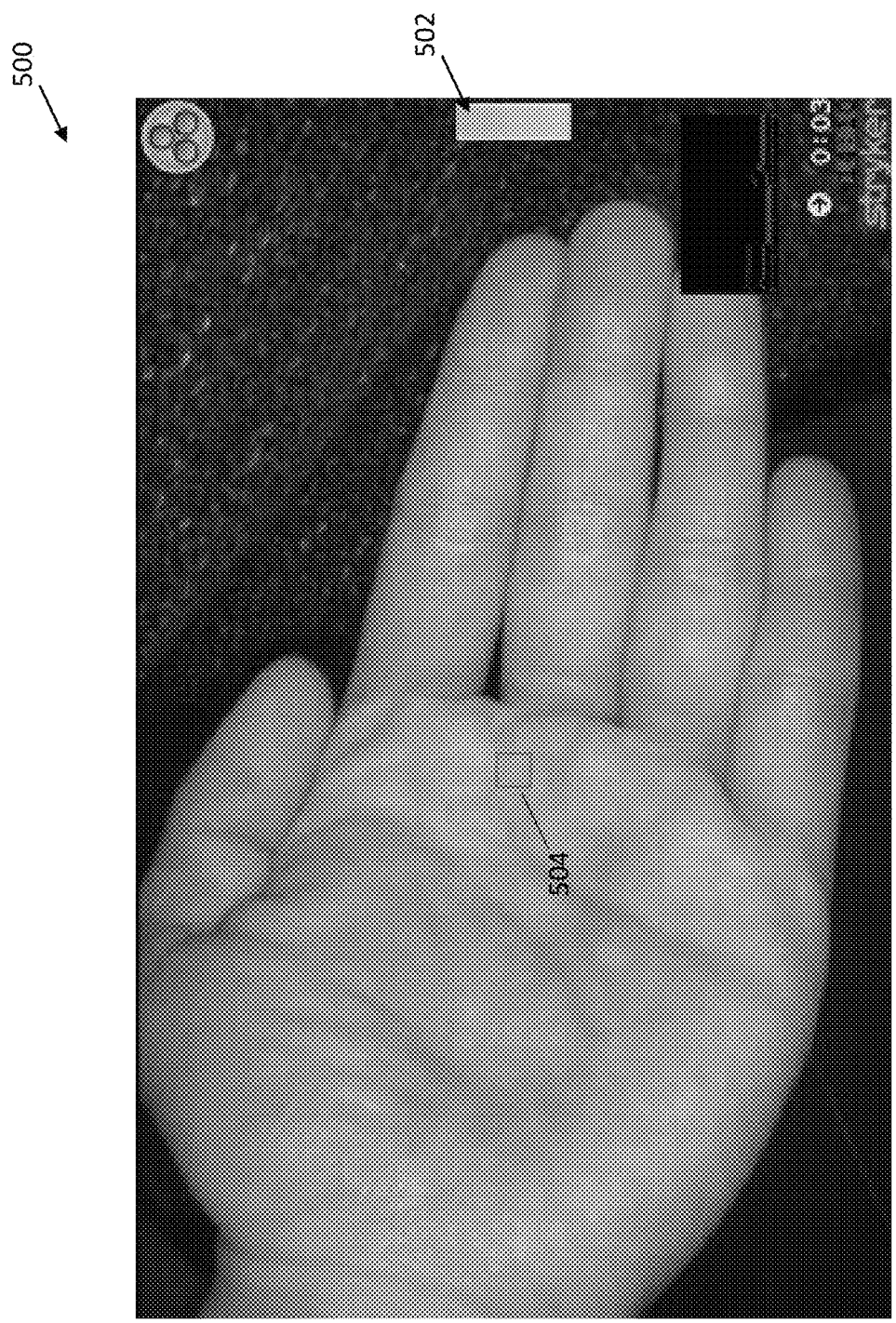
FIG. 5 illustrates an exemplary color map overlay prior to a user selection of a reference region.
Figure 6:
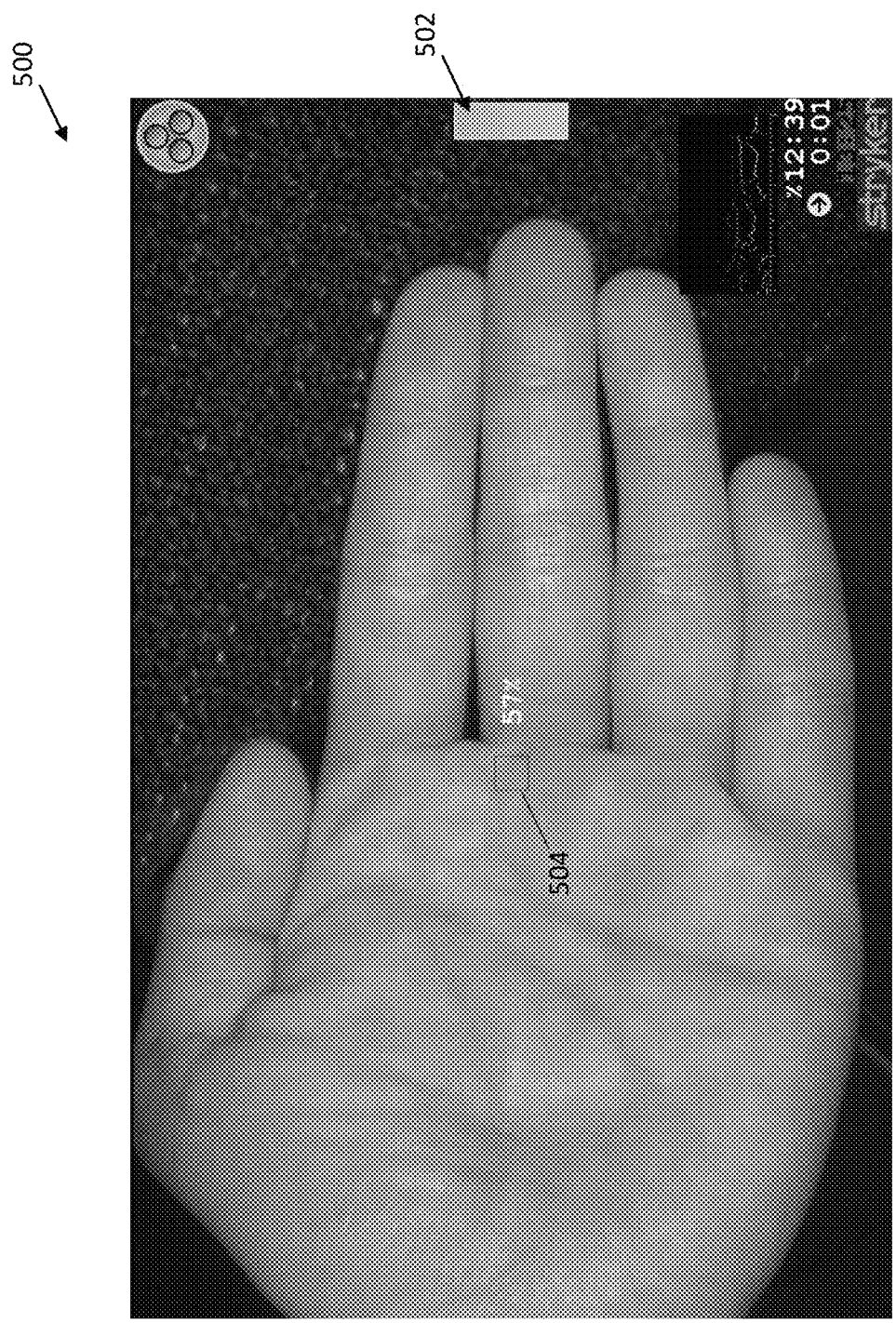
FIG. 6 illustrates the color map of FIG. 5 with the color scale adjusted based on a user selected reference region.

FIG. 5 illustrates graphical user interface 500 that includes an example of a color map generated from fluorescence imaging data displayed as an overlay on a visible light image. As shown in the color scale 502, the levels of highest fluorescence intensity are shown in red and the levels of lowest fluorescence intensity are shown in gray. A reference region selection guide indicator 504 is provided in the center of the field of view to assist the user in selecting the reference region. In this example, the user selects as a reference region an area associated with a relatively low fluoresce intensity. FIG. 6 illustrates the graphical user interface 500 in which the color map has been updated based on the color scale being adjusted according to the reference region selected by the user. In this example, the level of fluorescence intensity in the reference region is used to set an upper portion of the color scale 502, such that all areas of the field of view that are at the same or higher level of intensity as the reference region are shown in the red portion of the color scale.

Method 400 enables a user to at least partially define how different levels of fluorescence intensity are displayed, rather than being bound to a default display mode. For example, if the user is interested in portions of tissue that have relatively lower levels of intensity than some other areas within the field of view, the user may select a portion of the target region as a reference region and the reference level of intensity may be used as an upper bound of the color scale such that values above the reference level are clipped in terms of the color in which they are displayed. This can provide greater color gradation in the portion of tissue that the user is interested in. Conversely, the user may select as a reference region a portion of the field of view that the user deems to be noise or other low level intensity that is not of interest and the lower end of the color scale can be tied to that low level so that it appears the same color as zero intensity.

According to various aspects, the user can determine how the reference fluorescence intensity is used to define the color scale. For example, the user may be provided with options to set the lower bound, upper bound, middle, or any other point of the color scale based on the reference fluorescence intensity level.

Optionally, the color map may be automatically adjusted if the procedure has a predetermined associated color map. For example, if the procedure involves tissue on or near the liver, which typically may have a relatively high fluorescence intensity compared to surrounding tissues, then an associated color map may be used that helps to differentiate the liver from other fluorescence intensity levels so that differences in non-liver tissue fluorescence intensity levels can be easier to observe. In other examples, a different color map adjustment may be automatically applied for procedures in which visualization is more important than quantification.

Optionally, the color map may include a geometric scale in fluorescence intensity levels between colors (for example, a doubling of fluorescence intensity between colors may be used, such that the transition from the middle of blue on the color scale to the middle of green may indicate a doubling in FL intensity).

Optionally, the color map may include a linear scale between colors. Optionally, the color map may include a nonlinear scale between colors. Optionally, the color map may include a combination of one or more of a linear, a geometric, and a nonlinear portion of a scale in fluorescence intensity levels between colors.

Optionally, the bottom of the color map scale may correspond to a grey color, which can help to mask the appearance of noise in darker areas of the image.

Fluorescence imaging data as referred to herein can be generated by fluorescence imaging technologies employing a fluorescence imaging agent such as, for example, indocyanine green (ICG) dye as a fluorescence imaging agent. ICG, when administered to the subject, binds with blood proteins and circulates with the blood in the tissue. Although reference is made in the specification to a fluorescence agent or a fluorescence dye, other suitable imaging agents may be used depending on the type of imaging technology being employed to generate the time series of images.

In some variations, the fluorescence imaging agent (e.g., ICG) may be administered to the subject as a bolus injection, in a suitable concentration for imaging. In some variations where the method is performed to assess tissue perfusion, the fluorescence imaging agent may be administered to the subject by injection into a vein or artery of the subject such that the dye bolus circulates in the vasculature and traverses the microvasculature. In some variations in which multiple fluorescence imaging agents are used, such agents may be administered simultaneously (e.g., in a single bolus), or sequentially (e.g., in separate boluses). In some variations, the fluorescence imaging agent may be administered by a catheter. In some variations, the fluorescence imaging agent may be administered to the subject less than an hour in advance of performing the measurements for generating the time series of fluorescence images. For example, the fluorescence imaging agent may be administered to the subject less than 30 minutes in advance of the measurements. In other variations, the fluorescence imaging agent may be administered at least 30 seconds in advance of performing the measurements. In some variations, the fluorescence imaging agent may be administered contemporaneously with performing the measurements.

In some variations, the fluorescence imaging agent may be administered in various concentrations to achieve a desired circulating concentration in the blood. For example, in some variations for tissue perfusion assessment where the fluorescence imaging agent is ICG, the fluorescence imaging agent may be administered at a concentration of about 2.5 mg/mL to achieve a circulating concentration of about 5 µM to about 10 µM in blood. In some variations, the upper concentration limit for the administration of the fluorescence imaging agent is the concentration at which the fluorescence imaging agent becomes clinically toxic in circulating blood, and the lower concentration limit is the limit for instruments used to acquire the time series of fluorescence images that detect the fluorescence imaging agent circulating in blood. In some variations, the upper concentration limit for the administration of the fluorescence imaging agent is the concentration at which the fluorescence imaging agent becomes self-quenching. For example, the circulating concentration of ICG may range from about 2 µM to about 10 mM.

Thus, in one aspect, the method may comprise administration of a fluorescence imaging agent or other imaging agent to the subject, and generation or acquisition of the time series of fluorescence images prior to processing the image data. In another aspect, the method may exclude any step of administering the fluorescence imaging agent or other imaging agent to the subject. For instance, the time series of fluorescence images may be based on measurements of a fluorescence imaging agent such as, for example, indocyanine green (ICG) dye that is already present in the subject and/or based on autofluorescence response (e.g., native tissue autofluorescence or induced tissue autofluorescence), or measurements of a combination of autofluorescence and exogenous fluorescence arising from a fluorescence imaging agent.

In some variations, a suitable fluorescence imaging agent is an agent which can circulate with the blood (e.g., a fluorescence dye which can circulate with a component of the blood such as lipoproteins or serum plasma in the blood) and which fluoresces when exposed to appropriate excitation light energy. The fluorescence imaging agent may comprise a fluorescence dye, an analogue thereof, a derivative thereof, or a combination of these. A fluorescence dye may include any non-toxic fluorescence dye. In some variations, the fluorescence imaging agent optimally emits fluorescence in the near-infrared spectrum. In some variations, the fluorescence imaging agent is or comprises a tricarbocyanine dye such as, for example, indocyanine green (ICG). In other variations, the fluorescence imaging agent is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the fluorescence is derived from autofluorescence, one or more of the fluorophores giving rise to the autofluorescence may be an endogenous tissue fluorophore (e.g., collagen, elastin, NADH, etc.), 5-aminolevulinic Acid (5-ALA), or a combination thereof.

In some variations, the fluorescence imaging agent may be provided as a lyophilized powder, solid, or liquid. The fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. Any diluent or carrier which will maintain the fluorescence imaging agent in solution may be used. As an example, ICG may be reconstituted with water. In some variations, once the fluorescence imaging agent is reconstituted, it may be mixed with additional diluents and carriers. In some variations, the fluorescence imaging agent may be conjugated to another molecule, (e.g., a protein, a peptide, an amino acid, a synthetic polymer, or a sugar) so as to enhance solubility, stability, imaging properties or a combination thereof. Additional buffering agents may optionally be added including Tris, HCl, NaOH, phosphate buffer, HEPES.

In some variations, fluorescence imaging data comprises a plurality of individual image frames (e.g., fluorescence image frames), or data representative of individual frames, ordered consecutively by acquisition time. For example, fluorescence imaging data can include a time series of fluorescence images acquired using an ICG-based fluorescence imaging system, where the subject receives an intravenous injection of ICG immediately prior to a procedure, and the tissue is illuminated with light at ICG's excitation wavelengths while the resulting fluorescence emission from the dye as it transits the target tissue is imaged. The fluorescence images may subsequently also stored as a series of individual frames, or data representative of individual frames (e.g., compressed video), ordered consecutively by their acquisition time.

In some variations, the individual image frames of the time series are spatially aligned or registered. For example, a typical time series of fluorescence images may be recorded over 2 to 3 minutes, during which some subjects' movements may be unavoidable. As a result, the same anatomical features can appear at different positions in image frames acquired at different times during the image time series acquisition period. Since such misalignments can introduce errors in the subsequent analysis where the level of fluorescence for each pixel or a group of pixels is followed over time. To help reduce errors, the generated image frames may be spatially aligned (registered) with each other. In some variations, image registration or alignment refers to a process of determining the spatial transform that maps points from one image to homologous points in the second image.

Image registration may be an iterative process. For example, according to an exemplary embodiment, image registration may use one or more of the following set of components: two input images, a transform, a metric, an interpolator, and an optimizer. A transform maps the fixed image space into the moving image space. An optimizer is required to explore the parameter space Insight Segmentation and Registration Toolkit (ITK) (itk.org/) based implementation of the transform in search of optimal values of the metric may be used. The metric compares how well the two images match each other. Finally, the interpolator evaluates the intensities of the moving image at non-grid positions. To align the entire time series of fluorescence images, this procedure is executed for all the frames included in the analysis. The component loops through the range of input series frames, subtracts a background image for baseline correction and applies noise-reduction filters, then registers consecutive pairs of images.

Although various exemplary embodiments are described in the specification in the context of a time series of fluorescence images, the method may be applied to other sources of images generated as a time series which relate to a dynamic behavior of an imaging agent in the tissue and for other clinical purposes. For example, the images may be derived from computerized tomography (CT) angiography with a radio-opaque contrast dye for blood flow and tissue perfusion assessment. As another example, the images may be derived from positron emission tomography (PET) using a fluorodeoxyglucose (FDG) or other radiotracer to evaluate metabolic activity and potentially assess pathology and/or provide information usable for assessing pathology. As another example, the images may be derived from contrast-enhanced ultrasound imaging employing the use of gas-filled microbubble contrast medium administered intravenously to the systemic circulation. Such ultrasonic imaging using microbubble contrast agents enhances the ultrasound backscatter or reflection of the ultrasound waves to produce a unique sonogram with increased contrast due to the high echogenicity (i.e., ability of an object to reflect the ultrasound waves) difference between the gas in the microbubbles and the soft tissue. Contrast-enhanced ultrasound can be used, for example, to image blood perfusion and blood flow in organs.

System for Fluorescence Visualization

A system for fluorescence visualization, according to various aspects, can include an imaging system for acquiring at least one time series of images of tissue (e.g., a time series of fluorescence images, a time series of white light images, etc.), and one or more processors and memory having instructions stored thereon, wherein the instructions when executed by the one or more processors cause the system to perform the methods substantially as described above for fluorescence visualization.

Figure 7:
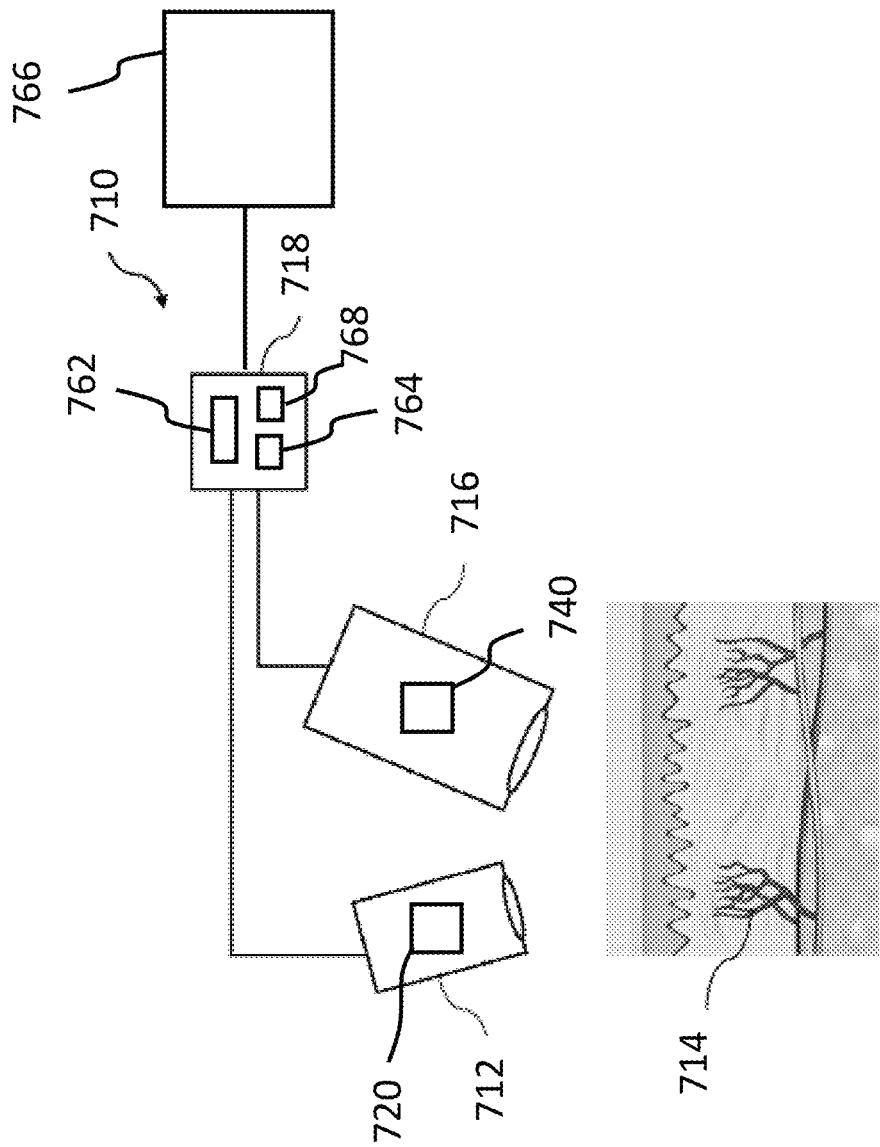
FIG. 7 is an illustrative depiction of an exemplary fluorescence imaging system.

In some variations, the system is a fluorescence imaging system. FIG. 7 is a schematic example of a fluorescence imaging system 710. The fluorescence imaging system 710 comprises a light source 712 to illuminate the tissue of the subject to induce fluorescence emission from a fluorescence imaging agent 714 in the tissue of the subject (e.g., in blood), an image acquisition assembly 716 arranged for generating the time series and/or the subject time series of fluorescence images from the fluorescence emission, and a processor assembly 718 arranged for processing the generated time series/subject time series of fluorescence images according to any of the variations of the methods described herein. The processor assembly 718 may include memory 768 with instructions thereon, a processor module 762 arranged for executing the instructions on memory 768 to process the time series and/or subject time series of fluorescence images as described herein in connection with the various embodiments of the methods, and a data storage module 764 to store the unprocessed and/or processed time series and/or subject time series of fluorescence images. In some variations, the memory 768 and data storage module 764 may be embodied in the same storage medium, while in other variations the memory 768 and the data storage module 764 may be embodied in different storage mediums. The system may further include a display 766 on which to display images and other data, such as some or all of a time series of fluorescence images or other input data, color maps, visual indications of relative fluorescence intensities, etc.

Figure 8:
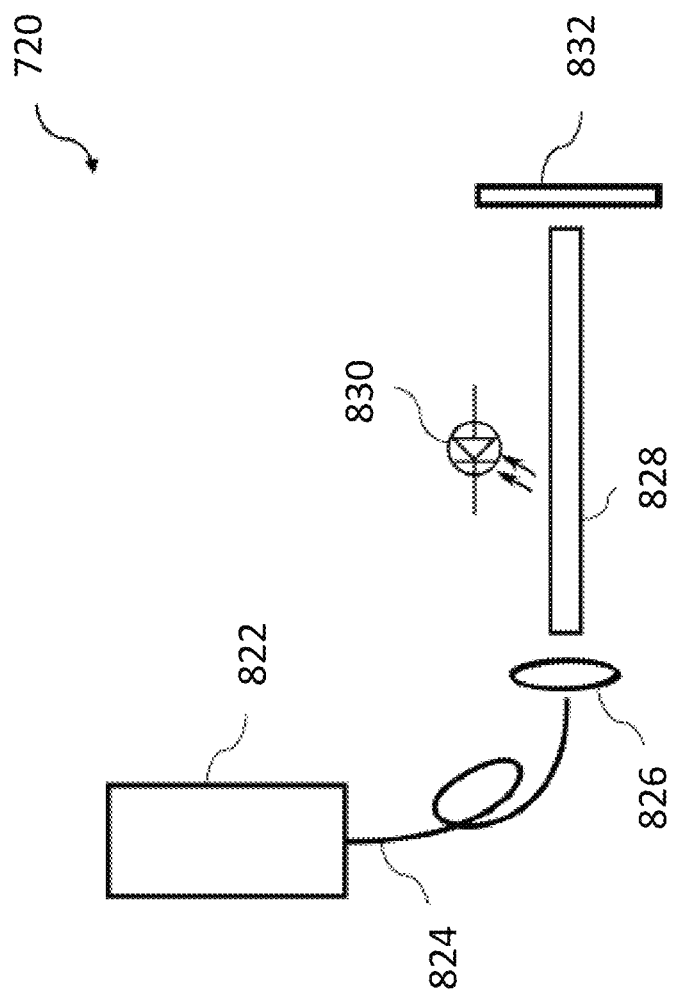
FIG. 8 is an illustrative depiction of an exemplary illumination module of a fluorescence imaging system.

In some variations, the light source 712 includes, for example, an illumination module 720. Illumination module 720 may include a fluorescence excitation source arranged for generating an excitation light having a suitable intensity and a suitable wavelength for exciting the fluorescence imaging agent 714. As shown in FIG. 8, the illumination module 720 may comprise a laser diode 822 (e.g., which may comprise, for example, one or more fiber-coupled diode lasers) arranged for providing an excitation light to excite the fluorescence imaging agent (not shown) in tissue of the subject. Examples of other sources of the excitation light which may be used in various embodiments include one or more LEDs, arc lamps, or other illuminant technologies of sufficient intensity and appropriate wavelength to excite the fluorescence imaging agent in the tissue. For example, excitation of the fluorescence imaging agent in blood, wherein the fluorescence imaging agent is a fluorescence dye with near infra-red excitation and emission characteristics, may be performed using one or more 793 nm, conduction-cooled, single bar, fiber-coupled laser diode modules from DILAS Diode Laser Co, Germany.

Referring again to FIG. 7, in some variations, the light output from the light source 712 may be projected through one or more optical elements to shape and guide the output being used to illuminate the tissue area of interest. The optical elements may include one or more lenses, light guides, and/or diffractive elements so as to ensure a flat field over substantially the entire field of view of the image acquisition assembly 716. The fluorescence excitation source may be selected to emit at a wavelength close to the absorption maximum of the fluorescence imaging agent 714 (e.g., ICG, etc.). For example, as shown in FIG. 8, the output 824 from the laser diode 822 may be passed through one or more focusing lenses 826, and then through a homogenizing light pipe 828 such as, for example, light pipes commonly available from Newport Corporation, USA. Finally, the light may be passed through an optical diffractive element 832 (i.e., one or more optical diffusers) such as, for example, ground glass diffractive elements also available from Newport Corporation, USA. Power to the laser diode 822 may be provided by, for example, a high-current laser driver such as those available from Lumina Power Inc. USA. The laser may optionally be operated in a pulsed mode during the image acquisition process. An optical sensor such as a solid state photodiode 830 may be incorporated into the illumination module 720 and may sample the illumination intensity produced by the illumination module 720 via scattered or diffuse reflections from the various optical elements. In some variations, additional illumination sources may be used to provide guidance when aligning and positioning the module over the area of interest.

Figure 9:
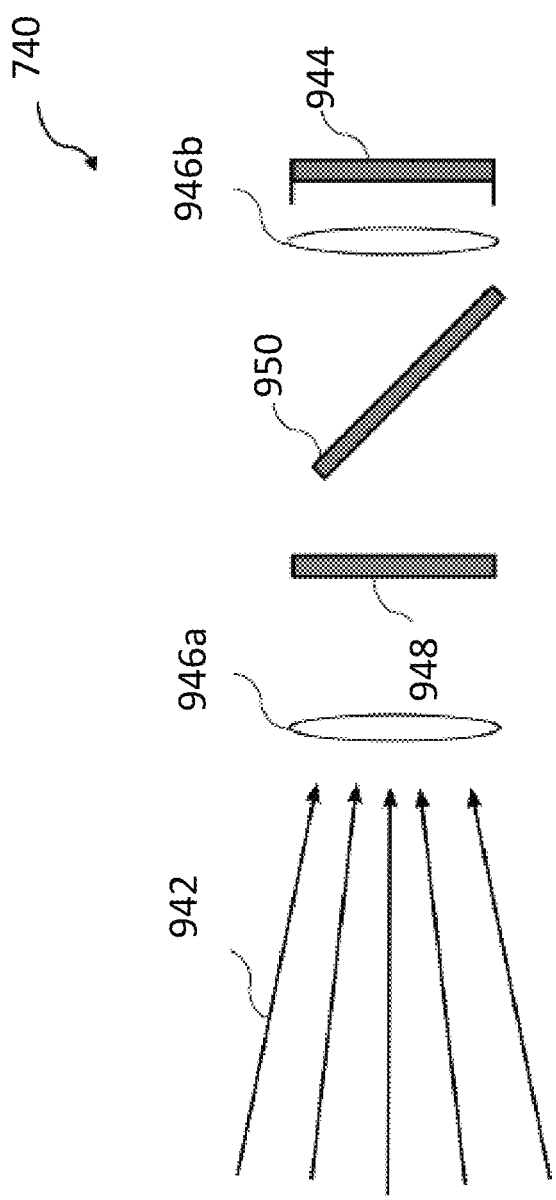
FIG. 9 is an exemplary camera module of an exemplary fluorescence imaging system, according to various aspects.

Referring again to FIG. 7, in some variations, the image acquisition assembly 716 may be a component of a fluorescence imaging system 710 configured to acquire the time series and/or subject time series of fluorescence images from the fluorescence emission from the fluorescence imaging agent 714. According to various aspects, the image acquisition assembly 716 can be or include an endoscopic imager, an open-field imager, a hand-held imager, or any other suitable imager. The image acquisition assembly 716 may include a camera module 740. As shown in FIG. 9, the camera module 740 may acquire images of the fluorescence emission 942 from the fluorescence imaging agent in the tissue by using a system of imaging optics (e.g., 946a, 946b, 948 and 950) to collect and focus the fluorescence emission onto an image sensor assembly 944. The image sensor assembly 944 may comprise at least one 2D solid state image sensor. The solid state image sensor may be a charge coupled device (CCD), a CMOS sensor, a CID or similar 2D sensor technology. The charge that results from the optical signal transduced by the image sensor assembly 944 is converted to an electrical video signal, which includes both digital and analog video signals, by the appropriate read-out and amplification electronics in the camera module 940.

According to an exemplary variation of a fluorescent imaging system, the light source may provide an excitation wavelength of about 800 nm+/−10 nm, and the image acquisition assembly uses emission wavelengths of >820 nm with NIR-compatible optics for, for example, ICG fluorescence imaging. In an exemplary embodiment, the NIR-compatible optics may include a CCD monochrome image sensor having a GigE standard interface and a lens that is compatible with the sensor with respect to optical format and mount format (e.g., C/CS mount).

In some variations, the processor module 762 comprises any computer or computing means such as, for example, a tablet, laptop, desktop, networked computer, or dedicated standalone microprocessor. For instance, the processor module 762 may include one or more central processing units (CPU). In an exemplary embodiment, the processor module 762 is a quad-core, 2.5 GHz processor with four CPUs where each CPU is a microprocessor such as a 64 -bit microprocessor (e.g., marketed as INTEL Core i3, i5, or i7, or in the AMD Core FX series). However, in other embodiments, the processor module 762 may be any suitable processor with any suitable number of CPUs and/or other suitable clock speed.

Inputs for the processor module 762 may be taken, for example, from the image sensor 944 of the camera module 740 shown in FIG. 9, from the solid state photodiode 830 in the illumination module 720 in FIG. 8, and/or from any external control hardware such as a footswitch or remote-control. Output is provided to the laser diode driver and optical alignment aids. As shown in FIG. 7, in some variations, the processor assembly 718 may have a data storage module 764 with the capability to save the time series/subject time series of images, or data representative thereof, or other input data to a tangible non-transitory computer readable medium such as, for example, internal memory (e.g. a hard disk or flash memory), so as to enable recording and processing of acquired data. In some variations, the processor module 762 may have an internal clock to enable control of the various elements and ensure correct timing of illumination and sensor shutters. In some variations, the processor module 762 may also provide user input and graphical display of outputs. The fluorescence imaging system may optionally be configured with a video display 766 or other monitor to display the time series of fluorescence images as they are being acquired or played back after recording. The video display 766 may additionally or alternatively visualize data generated during performance of the methods described herein, such as a spatial map, a subject spatial map, and/or tissue numerical value.

In operation of the exemplary system described in FIGS. 7-9, the subject is positioned relative to fluorescence imaging system 710 such that an area of interest (e.g., target tissue region) is located beneath the light source 712 and the image acquisition assembly 716 such that the illumination module 720 of light source 712 produces a substantially uniform field of illumination across substantially the entire area of interest. In some variations, prior to the administration of the fluorescence imaging agent 714 to the subject, an image may be acquired of the area of interest for the purposes of background deduction. To acquire fluorescence images/subject fluorescence images, the operator of the fluorescence imaging system 710 may initiate the acquisition of the time series of fluorescence images by depressing a remote switch or foot-control, or via a keyboard (not shown) connected to the processor assembly 718, or via a button or other user interface on a hand-held imager, such as a hand-held endoscopic imager or a hand-held open field imager. As a result, the light source 712 is turned on and the processor assembly 718 begins recording the fluorescence image data/subject fluorescence image data provided by the image acquisition assembly 716. When operating in a pulsed mode of the embodiment, the image sensor 944 in the camera module 740 is synchronized to collect fluorescence emission following the laser pulse produced by the diode laser 822 in the illumination module 720. In this way, maximum fluorescence emission intensity is recorded, and signal-to-noise ratio is optimized. In this embodiment, the fluorescence imaging agent 714 is administered to the subject and delivered to the area of interest via arterial flow. Acquisition of the time series of fluorescence images is initiated, for example, shortly after administration of the fluorescence imaging agent 714, and the time series of fluorescence images from substantially the entire area of interest is acquired throughout the ingress and egress of the fluorescence imaging agent 714. The fluorescence emission from the region of interest is collected by the collection optics of the camera module 740. Residual ambient and reflected excitation light is attenuated by subsequent optical elements (e.g., optical element 950 in FIG. 9 which may be a filter) in the camera module 740 so that the fluorescence emission can be acquired by the image sensor assembly 944 with minimal interference by light from other sources.

In some variations, following the acquisition or generation of at least a portion the time series of fluorescence images, the processor assembly 718 (e.g., processor module 762 or other processor) or one or more processors in communication with processor assembly 718 may then be initiated to execute instructions stored on memory 768 and perform one or more methods as described herein, including methods 100 and 400. The system 710 may visualize on display 766 fluorescence imaging-based visualizations, including a spatial map displayed to the user as, for example, a grayscale or false color image, and/or stored for subsequent use. Additionally or alternatively, the system 710 may display on display 766 one or more tissue numerical values, including numerical values associated with one or more regions of tissue selected by a user.

In some variations, the system for fluorescence visualization comprises a user interface, a processor arranged for communicating with the user interface, and a non-transitory computer-readable storage medium having instructions stored which, when executed by the processor, cause the processor to perform one or more of the methods for characterizing tissue and/or predicting a clinical data described herein. In some variations, the processor may be a component of the imaging system. In other variations, the processor may be located remotely from and in communication with an imaging system, where the imaging system may be the fluorescence imaging system described above, or any suitable imaging system.

A tangible non-transitory computer readable medium having computer-executable (readable) program code embedded thereon may provide instructions for causing one or more processors to, when executing the instructions, perform one or more of the methods described herein. Program code can be written in any appropriate programming language and delivered to the processor in many forms, including, for example, but not limited to information permanently stored on non-writable storage media (e.g., read-only memory devices such as ROMs, CD-ROM disks, etc.), information alterably stored on writable storage media (e.g., hard drives or the like), information conveyed to the processor through communication media, such as a local area network, a public network such as the Internet, or any type of media suitable for storing electronic instruction. When carrying computer readable instructions that implement the various embodiments of the method of the present invention, such computer readable media represent examples of various embodiments of the present invention. In various embodiments, the tangible non-transitory computer readable medium comprises all computer-readable media, and the present invention scope is limited to computer readable media wherein the media is both tangible and non-transitory.

A kit may include any part of the systems described herein and the fluorescence imaging agent such as, for example, a fluorescence dye such as ICG or any suitable fluorescence imaging agent. In further aspects, a kit may include a tangible non-transitory computer readable medium having computer-executable (readable) program code embedded thereon that may provide instructions for causing one or more processors, when executing the instructions, to perform one or more of the methods described herein. The kit may include instructions for use of at least some of its components (e.g., for using the fluorescence imaging agent, for installing the computer-executable (readable) program code with instructions embedded thereon, etc.). In yet further aspects, there is provided a fluorescence imaging agent such as, for example, a fluorescence dye for use in in the methods and systems described herein. In further variations, a kit may include any part of or the entire system described herein and a fluorescence agent such as, for example, a fluorescence dye such as ICG, or any other suitable fluorescence agent, or a combination of fluorescence agents.

Exemplary Imaging Agents

Optionally, a kit may include any part of the systems described herein and a fluorescence agent such as, for example, a fluorescence dye such as ICG or any suitable fluorescence agent or a combination of fluorescence agents. In some variations, a suitable fluorescence agent is an agent which can circulate with the blood (e.g., an agent which can circulate with, for example, a component of the blood such as plasma in the blood) and which fluoresces when exposed to appropriate excitation light energy. For example, ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. Optionally, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement. According to some embodiments, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 μM to about 10 μM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 µM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

According to some embodiments, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In various embodiments, the fluorescence imaging agent comprises a fluorescence dye, an analogue thereof, a derivative thereof, or a combination of these. An example of the fluorescence agent is a fluorescence dye, which includes any non-toxic fluorescence dye. In certain variations, the fluorescence dye may include a dye that emits light in the near-infrared spectrum. In certain embodiments, the fluorescence dye may include a tricarbocyanine dye such as, for example, indocyanine green (ICG). In other variations, the fluorescence dye may comprise methylene blue, ICG or a combination thereof In certain embodiments the dye is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the fluorescence is derived from autofluorescence, one or more of the fluorophores giving rise to the autofluorescence may be an endogenous tissue fluorophore (e.g., collagen, elastin, NADH, etc.), 5-aminolevulinic acid (5-ALA), or a combination thereof.

Optionally, the fluorescence imaging agent is configured to target a region of tissue and is used for visualizing the targeted region. The following is an exemplary list of imaging agents that can be used According to various aspects and the regions of tissue that they can target. ICG and/or Methylene blue may be used for targeting breast tissue, parathyroid tissue, and tumors. A proflavine agent can be used for targeting squamous cell neoplasia, Barrett's esophagus, colon polyps, dysplasia, anal dysplasia, head and neck cancer, cervical cancer, uterine cancer, oral disorders, and gastric cancer. ALA may be used for targeting gliomas, the bladder, and skin precancers and cancers. Hexaminolevulinate can be used for targeting the bladder, the cervix, and colorectal cancers. Methyl aminolevulinate can be used for targeting skin actinic keratosis, cancers, Bowen's disease, and acne. A cathepsin activatable can be used for targeting sarcomas, and colorectal, pancreatic, esophageal, breast, and prostate cancers. A protease activatable can be used for targeting breast cancer. Fluorescent lectin can be used for targeting colorectal cancer, neoplasms, and polyps. An HSP90 inhibitor can be used for targeting solid tumors. A chlorotoxin blocking chloride channels with Cy5.5 can be used for targeting gliomas, other CNS tumors, breast cancer, skin cancer, and sarcomas. A 7-aa peptide-IRDye800CW can be used for targeting gastrointestinal malignancies. A c-Met targeting peptide can be used for targeting colon cancer, esophageal cancer and high grade dysplasia, papillary thyroid cancer, and lung cancer. A folate receptor targeter can be used for targeting renal cell, lung, ovarian, pituitary, and pleural cancers. Tumor-specific integrin receptor binder can be used for targeting breast cancer. Anti-EGFR binding peptide can be used for targeting colon cancer and cholangiocarcinoma. Anti-EGFR affibody can be used for targeting gliomas, sarcomas, and head and neck cancers. GRPR receptor binding peptide can be used for targeting glioblastomas. VEGF antibody can be used for targeting esophageal cancer, breast cancer, and adenomatous polyposis. EGFR antibody can be used for targeting pancreatic cancer, brain neoplasms, gliomas, head and neck squamous cell carcinoma, and head and neck cancer. Carbonic anhydrase IX antibody can be used for targeting renal cell carcinomas.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. Optionally, once the fluorescence imaging agent is reconstituted, it may be mixed with additional diluents and carriers. Optionally, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although fluorescence imaging agents were described above in detail, other imaging agents may be used in connection with the systems, methods, and techniques described herein, depending on the medical imaging modality.

In some variations, the fluorescence imaging agent used in combination with the methods, systems and kits described herein may be used for blood flow imaging, tissue perfusion imaging, or a combination thereof, which may be performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems.

In variations relating to cardiac applications or any vascular applications, the imaging agent(s) (e.g., ICG alone or in combination with another imaging agent) may be injected intravenously. For example, the imaging agent may be injected intravenously through the central venous line, bypass pump and/or cardioplegia line and/or other vasculature to flow and/or perfuse the coronary vasculature, microvasculature and/or grafts. ICG may be administered as a dilute ICG/blood/saline solution down the grafted vessel or other vasculature such that the final concentration of ICG in the coronary artery or other vasculature depending on application is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. Optionally, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

One or more embodiments are directed to a fluorescence imaging agent for use in the imaging systems and methods as described herein. In one or more embodiments, the use may comprise vascular blood flow imaging, tissue perfusion imaging, or a combination thereof, which may occur during an invasive surgical procedure, a minimally invasive surgical procedure, a non-invasive surgical procedure, or a combination thereof. The fluorescence agent may be included in the kit described herein.

In one or more embodiments, the invasive surgical procedure may comprise a cardiac-related surgical procedure or a reconstructive surgical procedure. The cardiac-related surgical procedure may comprise a cardiac coronary artery bypass graft (CABG) procedure which may be on pump and/or off pump.

In one or more embodiments, the minimally invasive or the non-invasive surgical procedure may comprise a wound care procedure.

The methods and processes described herein may be performed by code or instructions to be executed by a computer, processor, manager, or controller, or in hardware or other circuitry. Because the algorithms that form the basis of the methods (or operations of the computer, processor, or controller) are described in detail, the code or instructions for implementing the operations of the method embodiments may transform the computer, processor, or controller into a special-purpose processor for performing the methods described herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the methods described herein.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for fluorescence imaging comprising:
receiving first fluorescence imaging data corresponding to a first fluorescence image captured during an imaging session, wherein the first fluorescence image is captured following the administration of a fluorescence imaging agent;

receiving a user input selecting a reference region associated with the first fluorescence imaging data;

determining a reference fluorescence intensity level based on the reference region and the first fluorescence imaging data;

receiving second fluorescence imaging data corresponding to a second fluorescence image captured during the imaging session while the fluorescence imaging agent is present in tissue associated with the reference region but after the first fluorescence image was captured;

determining a relative fluorescence intensity level of a region associated with the second fluorescence imaging data that is relative to the reference fluorescence intensity level determined based on the first fluorescence imaging data; and displaying an indication of the relative fluorescence intensity level.

2. The method of claim 1, wherein determining the reference fluorescence intensity level comprises determining a mean fluorescence intensity in the reference region and determining the relative fluorescence intensity level comprises determining a mean fluorescence intensity in the region associated with the second fluorescence imaging data.

3. The method of claim 1, comprising displaying a visualization based on the first fluorescence imaging data, wherein the user input selecting the reference region is a user input selecting a region of the visualization.

4. The method of claim 3, wherein the visualization comprises video.

5. The method of claim 3, wherein the visualization comprises fluorescence overlay on visible light imaging.

6. The method of claim 3, wherein receiving a user input selecting a reference region comprises locating a graphical selector at tissue captured in the first fluorescence imaging data to select a reference region of the tissue.

7. The method of claim 6, wherein the reference region of the tissue is healthy tissue.

8. The method of claim 1, wherein the indication of the relative fluorescence intensity level is a numerical indication.

9. The method of claim 1, comprising receiving third fluorescence imaging data and updating the indication of the relative fluorescence intensity level based on the third fluorescence imaging data.

10. The method of claim 1, further comprising providing an indication of when the reference fluorescence intensity level was determined.

11. The method of claim 1, wherein the first and second fluorescence imaging data include video frames.

12. The method of claim 1, further comprising determining multiple relative fluorescence intensity levels based on multiple regions associated with the second fluorescence imaging data.

13. The method of claim 1, wherein the reference region and the region associated with the second fluorescence imaging data are associated with the same region of tissue such that the relative fluorescence intensity level indicates a change in fluorescence intensity over time for the region of tissue.

14. The method of claim 1, wherein the first and second fluorescence imaging data is received from an imager during a medical procedure.

15. The method of claim 1, wherein the first and second fluorescence imaging data comprise normalized fluorescence intensity data.

16. The method of claim 1, wherein the user input selecting the reference region associated with the first fluorescence imaging data is received while fluorescence imaging agent is present in tissue associated with the reference region.

17. The method of claim 1, wherein the reference region and the region associated with the second fluorescence imaging data correspond to the same region of tissue.

18. A system for fluorescence imaging comprising:
one or more processors;
memory; and
one or more programs, wherein the one or more programs are stored in the memory and configured to be executed by the one or more processors, the one or more programs including instructions for:
receiving first fluorescence imaging data corresponding to a first fluorescence image captured during an imaging session, wherein the first fluorescence image is captured following the administration of a fluorescence imaging agent;
receiving a user input selecting a reference region associated with the first fluorescence imaging data;
determining a reference fluorescence intensity level based on the reference region and the first fluorescence imaging data;
receiving second fluorescence imaging data corresponding to a second fluorescence image captured during the imaging session while the fluorescence imaging agent is present in tissue associated with the reference region but after the first fluorescence image was captured;
determining a relative fluorescence intensity level of a region associated with the second fluorescence imaging data that is relative to the reference fluorescence intensity level determined based on the first fluorescence imaging data; and
displaying an indication of the relative fluorescence intensity level.

19. The system of claim 18, further comprising an imager for generating the first and second fluorescence imaging data.

20. The system of claim 18, further comprising an illuminator for generating fluorescence excitation light.

21. The system of claim 18, wherein selecting the target region comprises receiving a user input to select the target region.

22. The system of claim 18, wherein the first and second fluorescence imaging data comprise normalized fluorescence intensity data.

23. A non-transitory computer readable storage medium storing one or more programs for execution by one or more processors of a fluorescence imaging system, the one or more programs comprising instructions for:
receiving first fluorescence imaging data corresponding to a first fluorescence image captured during an imaging session, wherein the first fluorescence image is captured following the administration of a fluorescence imaging agent;
receiving a user input selecting a reference region associated with the first fluorescence imaging data;
determining a reference fluorescence intensity level based on the reference region and the first fluorescence imaging data;
receiving second fluorescence imaging data corresponding to a second fluorescence image captured during the imaging session while the fluorescence imaging agent is present in tissue associated with the reference region but after the first fluorescence image was captured;

determining a relative fluorescence intensity level of a region associated with the second fluorescence imaging data that is relative to the reference fluorescence intensity level determined based on the first fluorescence imaging data; and displaying an indication of the relative fluorescence intensity level.

* * * * *